United States Patent
Dorros et al.

(10) Patent No.: US 6,929,634 B2
(45) Date of Patent: Aug. 16, 2005

(54) APPARATUS AND METHODS FOR TREATING STROKE AND CONTROLLING CEREBRAL FLOW CHARACTERISTICS

(75) Inventors: Gerald Dorros, Scottsdale, AZ (US); Juan Carlos Parodi, Buenos Aires (AR); Mark C. Bates, Charleston, WV (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

(21) Appl. No.: 10/115,333

(22) Filed: Apr. 1, 2002

(65) Prior Publication Data

US 2003/0040705 A1 Feb. 27, 2003

Related U.S. Application Data

(63) Continuation-in-part of application No. 09/972,225, filed on Oct. 4, 2001.
(60) Provisional application No. 60/314,269, filed on Aug. 22, 2001.

(51) Int. Cl.$^7$ .............................................. A61M 25/00
(52) U.S. Cl. .................. 604/523; 604/96.01; 604/4.01; 604/6.16; 604/915; 606/194
(58) Field of Search ............................. 604/106, 96.01, 604/4.01, 6.1, 6.16, 507–510, 500, 264, 101.02, 523, 528, 915, 919, 103, 271; 606/159, 192, 167, 194

(56) References Cited

U.S. PATENT DOCUMENTS

| | | | | |
|---|---|---|---|---|
| 4,610,656 A | * | 9/1986 | Mortensen | .................. 604/6.14 |
| 4,706,671 A | * | 11/1987 | Weinrib | ...................... 606/159 |
| 4,921,478 A | | 5/1990 | Solano et al. | |
| 4,968,307 A | | 11/1990 | Dake et al. | |
| 4,994,069 A | | 2/1991 | Ritchart et al. | |
| 5,011,469 A | * | 4/1991 | Buckberg et al. | .......... 604/6.11 |
| 5,021,045 A | | 6/1991 | Buckberg et al. | |
| 5,425,723 A | | 6/1995 | Wang | |
| 5,643,228 A | | 7/1997 | Schucart et al. | |
| 5,713,853 A | | 2/1998 | Clark et al. | |
| 5,776,100 A | | 7/1998 | Forman | |
| 5,782,797 A | | 7/1998 | Schweich, Jr. et al. | |
| 5,794,629 A | | 8/1998 | Frazee | |
| 5,833,650 A | * | 11/1998 | Imran | ........................ 604/509 |

(Continued)

*Primary Examiner*—Cris L. Rodriguez

(57) ABSTRACT

Apparatus and methods for treatment of stroke are provided. In a preferred embodiment, the present invention disposes at least one catheter having a distal occlusive member in the common carotid artery of the hemisphere of the cerebral occlusion. Retrograde flow may be provided through the catheter to effectively control cerebral flow characteristics. Under such controlled flow conditions, a thrombectomy device may be used to treat the occlusion, and any emboli generated are directed into the catheter.

22 Claims, 11 Drawing Sheets

U.S. PATENT DOCUMENTS

| | | | |
|---|---|---|---|
| 5,895,398 A | | 4/1999 | Wensel et al. |
| 5,908,407 A | | 6/1999 | Frazee et al. |
| 5,919,163 A | | 7/1999 | Glickman |
| 5,941,896 A | | 8/1999 | Kerr |
| 5,954,737 A | * | 9/1999 | Lee .......................... 606/159 |
| 5,972,019 A | * | 10/1999 | Engelson et al. ........... 606/200 |
| 6,017,493 A | * | 1/2000 | Cambron et al. ............. 422/44 |
| 6,022,336 A | * | 2/2000 | Zadno-Azizi et al. .. 604/101.05 |
| 6,044,845 A | | 4/2000 | Lewis |
| 6,059,745 A | | 5/2000 | Gelbfish |
| 6,066,149 A | * | 5/2000 | Samson et al. ............. 606/159 |
| 6,066,158 A | | 5/2000 | Engelson et al. |
| 6,105,582 A | | 8/2000 | Pranevicius et al. |
| 6,110,139 A | | 8/2000 | Loubser |
| 6,135,991 A | | 10/2000 | Muni et al. |
| 6,146,370 A | * | 11/2000 | Barbut ........................ 604/500 |
| 6,152,946 A | | 11/2000 | Broome et al. |
| 6,161,547 A | | 12/2000 | Barbut |
| 6,165,199 A | | 12/2000 | Barbut |
| 6,203,561 B1 | * | 3/2001 | Ramee et al. ............... 606/200 |
| 6,231,551 B1 | | 5/2001 | Barbut |
| 6,241,699 B1 | * | 6/2001 | Suresh et al. .................. 604/7 |
| 6,264,672 B1 | * | 7/2001 | Fisher ......................... 606/200 |
| 6,348,056 B1 | | 2/2002 | Bates et al. |
| 6,361,545 B1 | | 3/2002 | Macoviak et al. |
| 6,413,235 B1 | * | 7/2002 | Parodi ......................... 604/104 |
| 6,419,686 B1 | | 7/2002 | McLeod et al. |
| 6,423,032 B2 | * | 7/2002 | Parodi ................... 604/103.07 |
| 6,435,189 B1 | * | 8/2002 | Lewis et al. ................. 128/898 |
| 6,436,112 B2 | * | 8/2002 | Wensel et al. .............. 606/159 |
| 6,454,775 B1 | | 9/2002 | Demarais et al. |
| 6,458,139 B1 | | 10/2002 | Palmer et al. |
| 6,468,291 B2 | | 10/2002 | Bates et al. |
| 6,485,502 B2 | * | 11/2002 | Don Michael et al. ..... 606/200 |
| 6,511,492 B1 | * | 1/2003 | Rosenbluth et al. ........ 606/159 |
| 6,533,770 B1 | * | 3/2003 | Lepulu et al. ............... 604/524 |
| 6,540,712 B1 | * | 4/2003 | Parodi et al. .............. 604/6.14 |
| 6,544,279 B1 | * | 4/2003 | Hopkins et al. ............. 606/200 |
| 6,595,963 B1 | * | 7/2003 | Barbut ........................ 604/246 |
| 6,620,148 B1 | * | 9/2003 | Tsugita ....................... 604/509 |
| 6,632,236 B2 | * | 10/2003 | Hogendijk .................. 606/198 |
| 6,638,293 B1 | | 10/2003 | Makower et al. |
| 6,645,222 B1 | * | 11/2003 | Parodi et al. ................ 606/200 |
| 6,673,042 B1 | * | 1/2004 | Samson et al. ............. 604/104 |
| 2002/0165573 A1 | * | 11/2002 | Barbut ........................ 606/194 |
| 2003/0163158 A1 | * | 8/2003 | White ......................... 606/200 |
| 2003/0191448 A1 | * | 10/2003 | Swindle ...................... 604/509 |

* cited by examiner

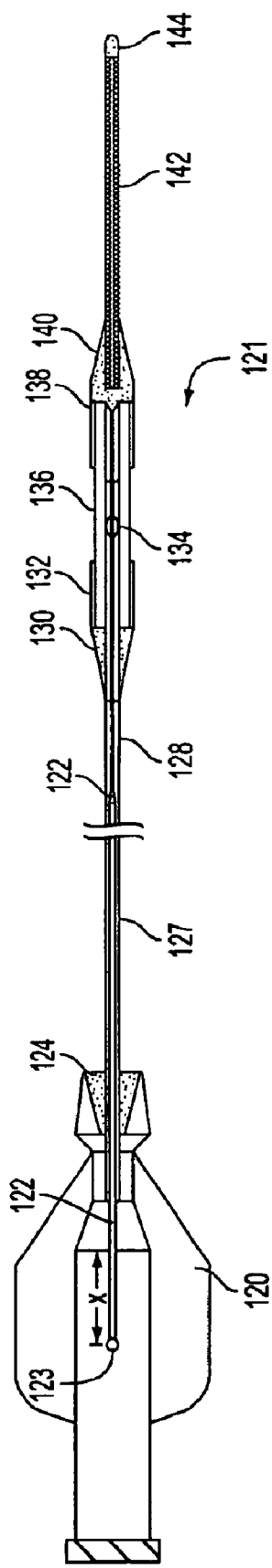
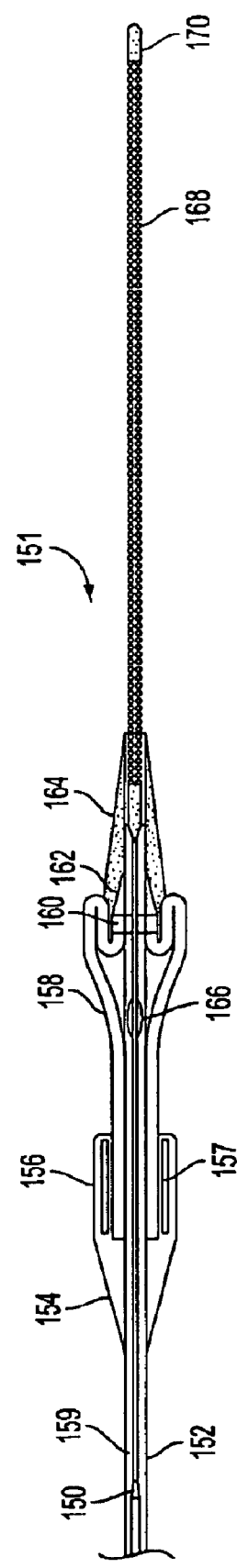
FIG. 4A
FIG. 4B

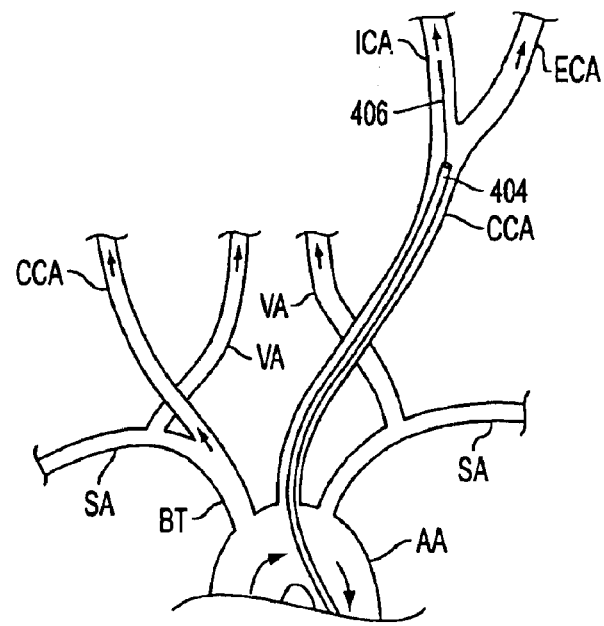
FIG. 7A
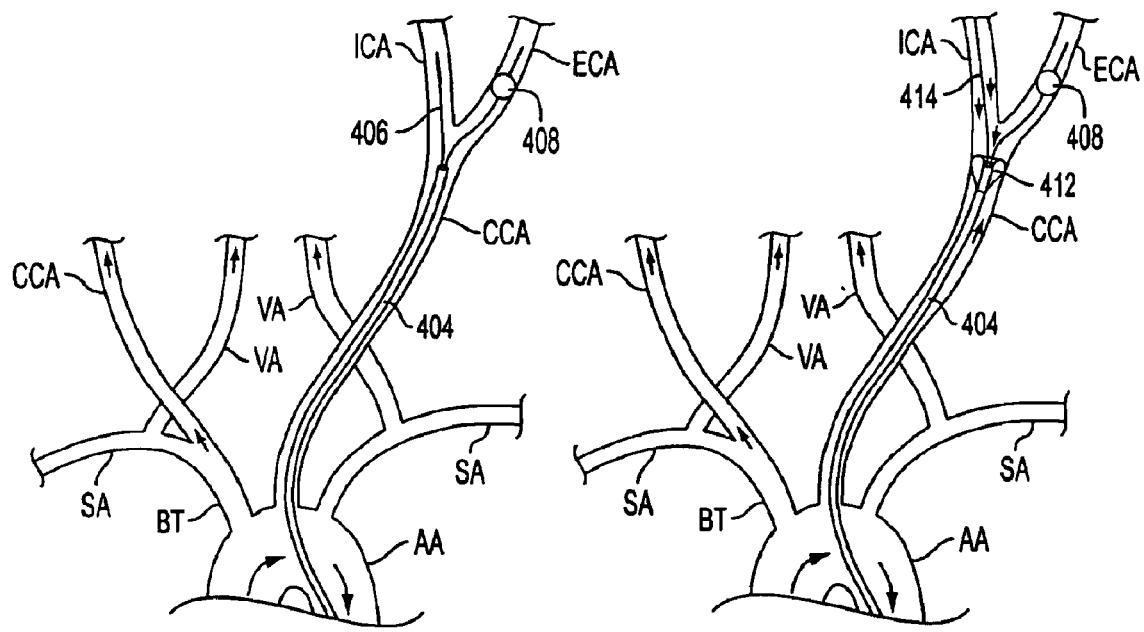
FIG. 7B
FIG. 7C

APPARATUS AND METHODS FOR TREATING STROKE AND CONTROLLING CEREBRAL FLOW CHARACTERISTICS

REFERENCE TO RELATED APPLICATION

The present application is a continuation-in-part of U.S. patent application Ser. No. 09/972,225, filed Oct. 4, 2001.

FIELD OF THE INVENTION

The present invention relates to improved apparatus and methods for treatment of stroke. More specifically, the apparatus and methods of the present invention are directed to treating stroke by controlling cerebral blood flow and removing thrombi and/or emboli.

BACKGROUND OF THE INVENTION

Cerebral occlusions that lead to stroke require swift and effective therapy to reduce morbidity and mortality rates associated with the disease. Many current technologies for treating stroke are inadequate because emboli generated during the procedure may travel downstream from the original occlusion and cause ischemia. There is currently a need for a stroke treatment system that provides a swift and efficient treatment for occlusions while simultaneously controlling cerebral flow characteristics.

In the initial stages of stroke, a CT scan or MRI may be used to diagnose the cerebral occlusion, which commonly occurs in the middle cerebral arteries. Many current technologies position a catheter proximal to the occlusion, then deliver clot dissolving drugs to treat the lesion. A drawback associated with such technology is that delivering drugs may require a period of up to six hours to adequately treat the occlusion. Another drawback associated with lytic agents (i.e., clot dissolving agents) is that they often facilitate bleeding.

When removing thrombus using mechanical embolectomy devices, it is beneficial to engage the thrombus and remove it as cleanly as possible, to reduce the amount of emboli that are liberated. However, in the event that emboli are generated during mechanical disruption of the thrombus, it is imperative that they be subsequently removed from the vasculature.

Many current drug delivery and mechanical treatment methods are performed under antegrade flow conditions. Such treatment methods do not attempt to manipulate flow characteristics in the cerebral vasculature, e.g., the Circle of Willis and communicating vessels, such that emboli may be removed. Accordingly, there remains a need to provide effective thrombus and emboli removal from the cerebral vasculature while simultaneously controlling flow within that vasculature.

U.S. Pat. No. 6,161,547 to Barbut (Barbut '547) describes a technique for enhancing flow in the cerebral vasculature in treating patients with acute stroke or other cerebrovascular disease. The technique involves: (1) positioning a first tubular member in a vascular location suitable for receiving antegrade blood flow; (2) positioning a second tubular member in a contralateral artery of the occlusion (e.g., for an occlusion located in the left common carotid artery the second tubular member is placed in the right common carotid artery); and coupling the first tubular member to the second tubular member using a pump and filter.

The first tubular member receives antegrade blood flow and channels the blood to the pump and filter, where the blood then is reperfused via the second tubular member into the contralateral artery, thus increasing blood flow to the opposing hemisphere of the brain. The first and second tubular members may include balloons disposed adjacent to their distal ends.

The techniques described in the foregoing patent have several drawbacks. For example, if the first balloon of the first tubular member is deployed in the left common carotid artery, as shown in FIG. 7C of that patent, aspiration of blood from the vessel between the balloon and the occlusion may cause the vessel to collapse. On the other hand, if the balloon is not deployed, failure to stabilize the distal tip may result in damage to the vessel walls. In addition, failure to occlude the vessel may permit antegrade blood flow to be diverted into that apparatus, rather than blood distal to the first tubular member.

The Barbut '547 patent further discloses that inflating the balloon of the second tubular member may assist in controlling the flow to the contralateral artery or provide more efficient administration of pharmacotherapy to the cerebral tissues. However, when that balloon is deployed, the contralateral artery may be starved of sufficient flow, since the only other flow in that artery is that aspirated through the first tubular member. On the other hand, if the balloon of the second tubular member is not inflated, no flow control is possible.

A method for removing cerebral occlusions is described in U.S. Pat. No. 6,165,199 to Barbut (Barbut '199). This patent describes a catheter having an aspiration port at its distal end that communicates with a vacuum at its proximal end. A perfusion port disposed in a lateral surface of the catheter may be used to enhance antegrade flow in collateral arteries. In use, the aspiration port is positioned proximal to an occlusion to provide a direct suction effect on the occlusion. The perfused flow in collateral arteries is intended to augment retrograde flow distal to the occlusion, such that the occlusion is dislodged via the pressure and directed toward the aspiration port. A chopping mechanism, e.g., an abrasive grinding surface or a rotatable blade, coupled to the aspiration port recognizes when the aspiration port is clogged. The chopping mechanism then engages to break up the occlusion and permit it to enter the aspiration port in smaller pieces.

The device described in the Barbut '199 patent has several disadvantages. First, the use of a vacuum to aspirate the occlusion requires an external pressure monitoring device. The application of too much vacuum pressure through the aspiration port may cause trauma, i.e., collapse, to the vessel wall. Also, because the system is intended to dislodge the occlusion using a pressure differential, a chopping mechanism is required to prevent the entire mass from clogging the aspiration port. The use of a chopping mechanism, however, may generate such a large quantity of emboli that it may be difficult to retrieve all of the emboli. In addition, emboli generated by the action of the chopping mechanism may accumulate alongside the catheter, between the aspiration port and the distal balloon. Once this occurs, it is unclear how the emboli will be removed.

Yet another drawback of the device described in the Barbut '199 patent is that high-pressure perfusion in collateral arteries may not augment retrograde flow distal to the occlusion as hypothesized. The patent indicates that high-pressure perfusion in collateral arteries via side ports in the catheter may be sufficient to cause an increase in pressure distal to the occlusion. Antegrade blood flow from the heart in unaffected arteries, e.g., other vertebral and/or carotid arteries, may make it difficult for the pressure differential induced in the contralateral arteries to be communicated back to the occluded artery in a retrograde fashion.

Other methods for treating ischemic brain stroke have involved cerebral retroperfusion techniques. U.S. Pat. No. 5,794,629 to Frazee describes a method that comprises at least partially occluding the first and second transverse venous sinuses and introducing a flow of the patient's arterial blood to a location distal to the partial venous occlusions. As described in that patent, the infusion of arterial blood into the venous sinuses provides a retrograde venous flow that traverses the capillary bed to oxygenate the ischemic tissues and at least partially resolve ischemic brain symptoms.

One drawback associated with the technique described in the Frazee patent is that the pressure in the transverse venous sinuses must be continuously monitored to ensure that cerebral edema is avoided. Because the veins are much less resilient than arteries, the application of sustained pressure on the venous side may cause brain swelling, while too little pressure may result in insufficient blood delivered to the arterial side.

In addition to the foregoing methods to augment cerebral perfusion, several methods are known for mechanically removing clots to treat cerebral occlusions. U.S. Pat. No. 5,895,398 to Wensel et al. (Wensel) describes a shape-memory coil affixed to an insertion mandrel. The coil is contracted to a reduced profile state within the lumen of a delivery catheter, and the catheter is used to cross a clot. Once the coil is disposed distal to the clot, the coil is deployed. The coil then is retracted proximally to engage and remove the clot.

A primary drawback associated with the device described in the Wensel patent is that the deployed coil contacts the intima of the vessel, and may damage to the vessel wall when the coil is retracted to snare the occlusion. Additionally, the configuration of the coil is such that the device may not be easily retrieved once it has been deployed. For example, once the catheter has been withdrawn and the coil deployed distal to the occlusion, it may be difficult or impossible to exchange the coil for another of different dimensions.

U.S. Pat. No. 5,972,019 to Engelson et al. (Engelson) describes a deployable cage assembly that may be deployed distal to a clot. Like the Wensel device, the device described in the Engelson patent is depicted as contacting the intima of the vessel, and presents the same risks as the Wensel device. In addition, because the distal end of the device comprises a relatively large profile, the risk of dislodging emboli while crossing the clot is enhanced, and maneuverability of the distal end of the device through tortuous vasculature may be reduced.

In view of these drawbacks of previously known clot removal apparatus and methods, it would be desirable to provide apparatus and methods for controlling hemodynamic properties at selected locations in the cerebral vasculature, e.g., the Circle of Willis and communicating vessels.

It also would be desirable to provide apparatus and methods for removal and recovery of thrombi and/or emboli above the carotid bifurcation.

It still further would be desirable to provide apparatus and methods that quickly and efficiently treat cerebral occlusions.

SUMMARY OF THE INVENTION

In view of the foregoing, it is an object of the present invention to provide apparatus and methods for controlling hemodynamic properties at selected locations in the cerebral vasculature.

It is also an object of the present invention to provide apparatus and methods for removal and recovery of thrombi and/or emboli above the carotid bifurcation.

It is a further object of the present invention to provide apparatus and methods that quickly and efficiently treat cerebral occlusions.

These and other objects of the present invention are accomplished by providing a stroke treatment system comprising an emboli removal catheter suitable for manipulating blood flow in the cerebral vasculature. The stroke treatment system may facilitate the introduction of clot lysing agents alone or in conjunction with a thrombectomy element.

In a preferred embodiment, the emboli removal catheter is transluminally inserted and disposed in the common carotid artery CCA, and comprises a flexible catheter having an occlusive member disposed on its distal end. The occlusive member is configured to be deployed to anchor the catheter and occlude antegrade flow in the CCA. Optionally, a separate occlusive element that is configured to pass through a lumen of the emboli removal catheter may be deployed in the external carotid artery ECA to occlude flow through that vessel. When the emboli removal catheter is deployed in the CCA and used in conjunction with the occlusive element deployed in the ECA, flow characteristics in the cerebral vasculature, including flow in the middle cerebral artery MCA, may be influenced by the flow through the lumen of the emboli removal catheter.

With flow controlled at the selected cerebral locations, the distal end of a thrombectomy element then may be advanced across the lesion. Lytic agents may be infused directly into the lesion via a drug delivery lumen of an outer sheath that contains the thrombectomy element in a contracted state. After the lytic agents have been infused for a desired time, the thrombectomy element may be self-deployed distal to the occlusion by proximally retracting the outer sheath. The thrombectomy element then may be retracted to snare a remaining portion of the lesion, i.e., a portion that was not removed via the lytic process, and the thrombectomy element then is retracted into the emboli removal catheter. Because retrograde or redistributed flow has been generated in the cerebral vasculature, emboli liberated during the lytic process and/or actuation of the thrombectomy element are directed into the emboli removal catheter for removal.

BRIEF DESCRIPTION OF THE DRAWINGS

Further features of the invention, its nature and various advantages will be more apparent from the accompanying drawings and the following detailed description of the preferred embodiments, in which:

FIGS. 4A–4B are views of alternative embodiments of low profile occlusive elements for occluding flow in the external carotid arteries;

FIGS. 7A–7E illustrate method steps for controlling cerebral blood flow and removing thrombi and/or emboli in accordance with the present invention.

DETAILED DESCRIPTION OF THE INVENTION

Figure 1:
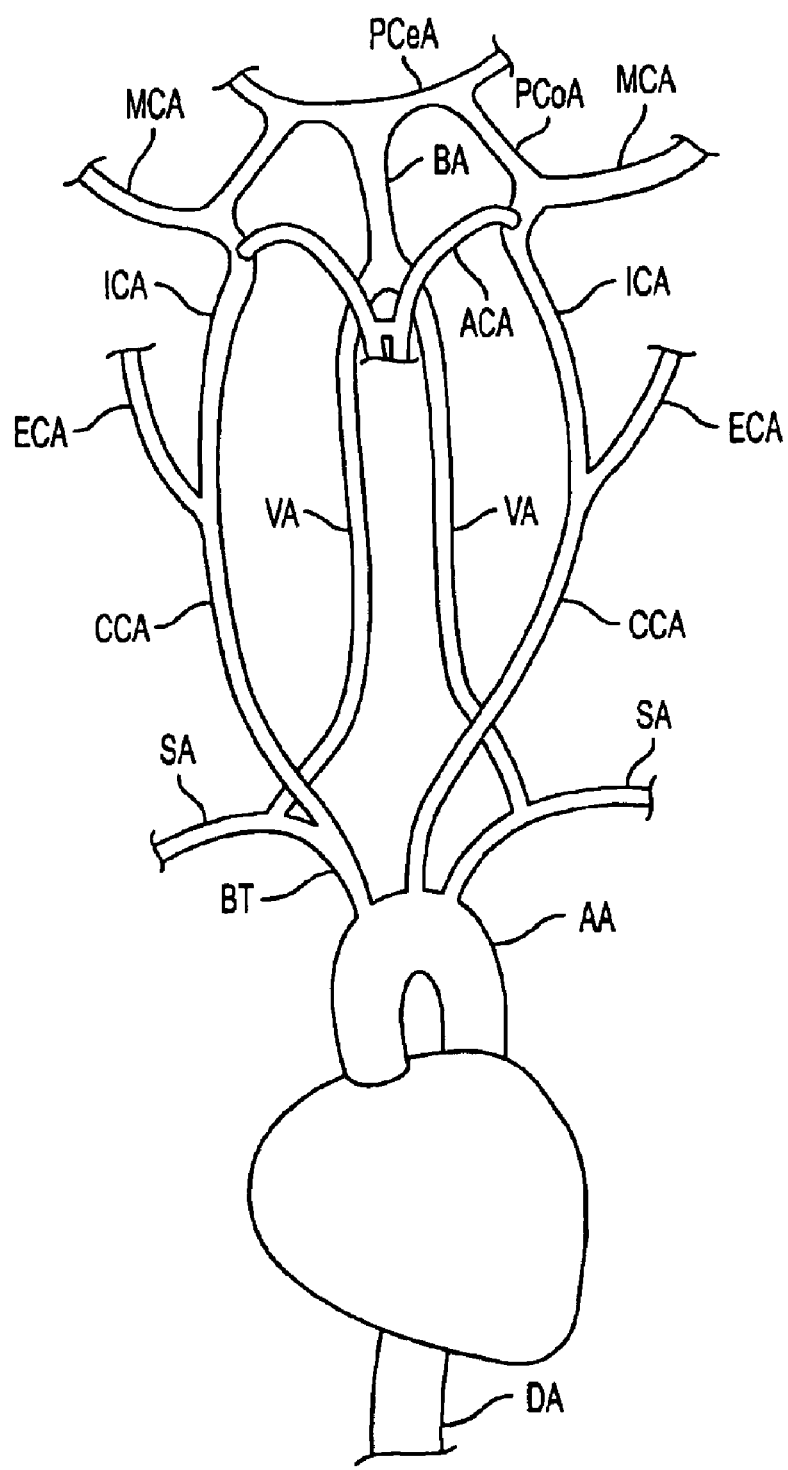
FIG. 1 provides a schematic overview of the portion of the vasculature in which the apparatus and methods of the present invention are intended for use.

Referring to FIG. 1, a schematic of the pertinent vasculature relating to the present invention is provided. Many cerebral obstructions that lead to stroke reside in the middle cerebral arteries MCA. To treat obstructions in the MCA, one approach involves percutaneously and transluminally advancing a therapeutic device to the site of the obstruction via the internal carotid artery ICA.

It is well known in the art to percutaneously and transluminally advance a catheter in retrograde fashion toward coronary vasculature, e.g., via the femoral artery, external iliac artery, descending aorta DA and aortic arch AA. To access cerebral vasculature, including obstructions residing in the MCA, one approach is to further advance a catheter and/or therapeutic devices in antegrade fashion from the aortic arch AA, into the common carotid artery CCA, up through the ICA and into the middle cerebral artery MCA, as shown in FIG. 1.

Treating occlusions in the MCA may generate emboli upon removal of the occlusion. Under normal blood flow conditions, such emboli may travel downstream from the original occlusion and cause ischemia. Accordingly, it is advantageous to manipulate blood flow characteristics in the cerebral vasculature to ensure that emboli generated in the MCA are effectively removed.

Figure 2:
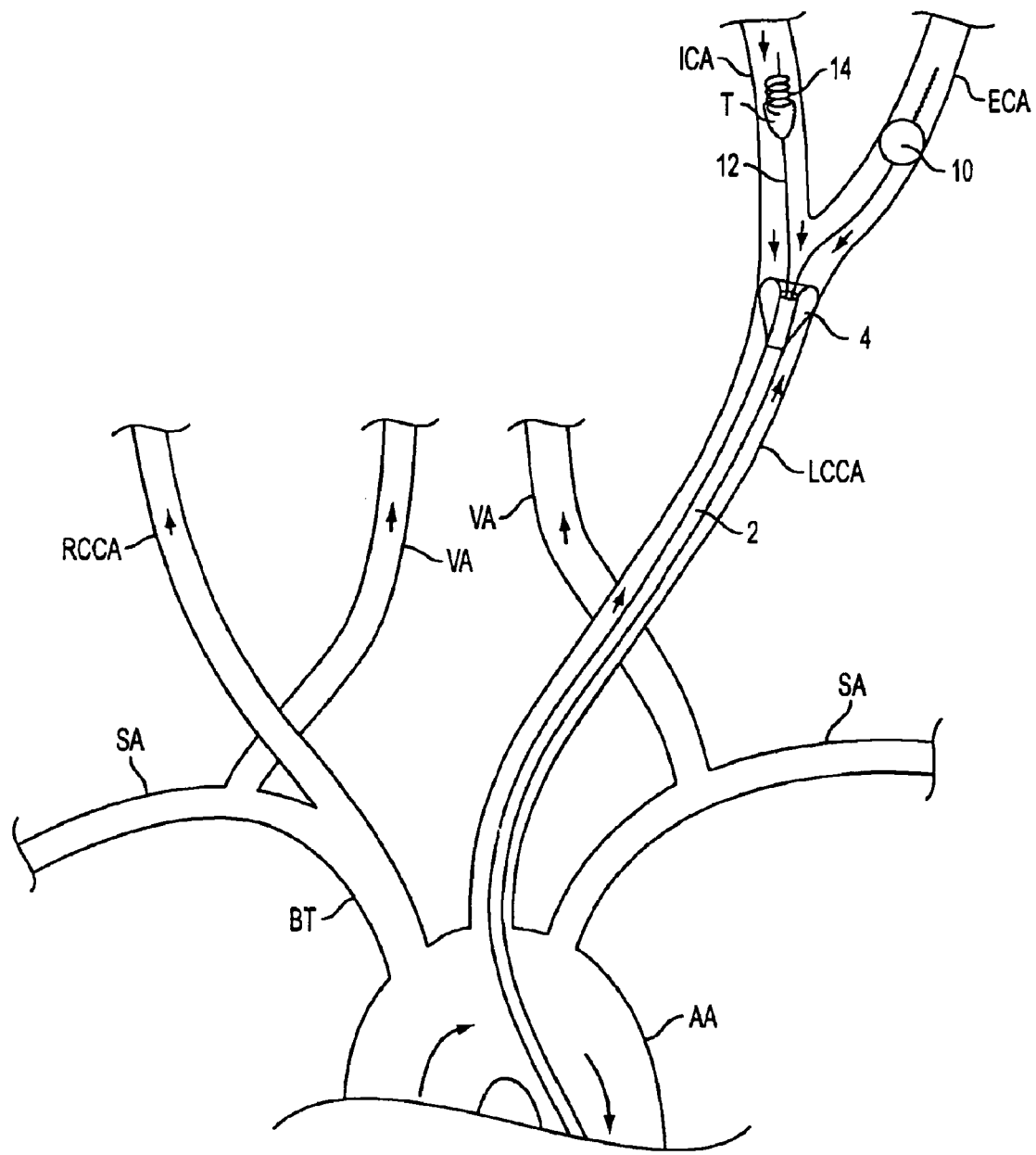
FIG. 2 provides an overview of the apparatus of the present invention deployed in a patient's vasculature.

FIG. 2 provides an overview of the components of the system of the present invention, each of which are described in greater detail hereinbelow. Emboli removal catheter 2 includes distal occlusive element 4, and is configured to be percutaneously advanced in retrograde fashion through the descending aorta. Occlusive element 4 preferably comprises a pear-shaped or funnel-shaped balloon as described in co-pending and commonly assigned U.S. patent application Ser. No. 09/418,727, which is incorporated herein by reference. Occlusive element 4 preferably is positioned proximal to the carotid bifurcation, and then deployed to induce retrograde flow in the ICA by use of a venous return catheter (not shown) that communicates with the proximal end of catheter 2. Balloon 10, also described in the foregoing application, is deployed in the ECA to ensure that retrograde flow from the ECA is not carried in an antegrade fashion into the ICA.

Applicant has determined that when occlusive element 4 is deployed proximal to the carotid bifurcation, and balloon 10 is deployed in the ECA, the retrograde flow induced in the ICA by use of the venous return catheter (described hereinbelow with respect to FIG. 3A) is sufficient to manipulate flow in the cerebral vasculature, and more specifically, in the MCA. Moreover, balloon 10 may be omitted in the case where the ECA already has been sufficiently occluded by an existing vascular occlusion, in which case emboli removal catheter 2 may be used alone to influence cerebral flow. Emboli removal catheter 2 may used to suspend antegrade flow in the cerebral arteries and to selectively suspend or redistribute flow in the cerebral vasculature.

In FIG. 2, thrombectomy wire 12 comprises knot 14 that is deployed distal to the thrombus T. Thrombectomy wire 12 and thrombus T then are retracted proximally into the lumen of emboli removal catheter 2, and any embolic fragments generated during this procedure are directed into catheter 2 by inducing cerebral retrograde flow.

Figure 3A:
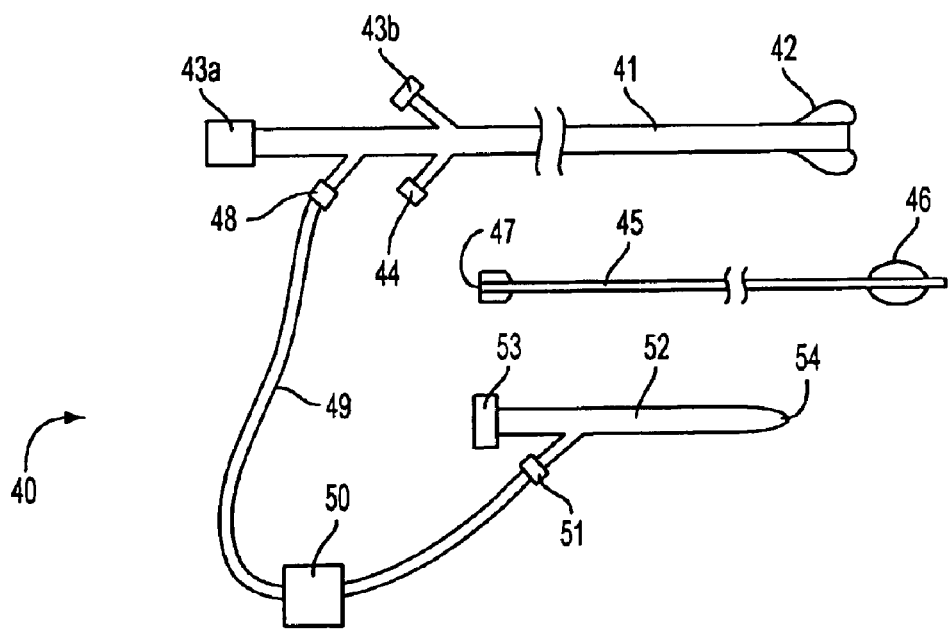
FIGS. 3A–3D are, respectively, a schematic view of apparatus in accordance with the present invention, detailed side and sectional views of the distal end of an emboli removal catheter of the present invention, and a cross-sectional view of the emboli removal catheter.

Referring now to FIG. 3A, stroke treatment apparatus 40 constructed in accordance with the principles of the present invention is described. Apparatus 40 comprises emboli removal catheter 41, wire 45, venous return line 52, tubing 49 and optional blood filter 50.

Catheter 41 includes distal occlusive element 42, hemostatic ports 43a and 43b, e.g., Touhy-Borst connectors, inflation port 44, and blood outlet port 48. Wire 45 includes balloon 46 that is inflated via inflation port 47. Tubing 49 couples blood outlet port 48 to filter 50 and blood inlet port 51 of venous return line 52.

Wire 45 preferably comprises a small diameter flexible shaft having an inflation lumen that couples inflatable balloon 46 to inflation port 47. Wire 45 and balloon 46 are configured to pass through hemostatic ports 43a and 43b and the aspiration lumen of catheter 41 (see FIGS. 3C and 3D), so that balloon 46 may be disposed in a communicating artery, e.g., the external carotid artery. Ports 43a and 43b and the aspiration lumen of catheter 41 are sized to permit additional interventional devices, such as thrombectomy wires, to be advanced through the aspiration lumen when wire 45 is deployed.

Venous return line 52 includes hemostatic port 53, blood inlet port 51 and a lumen that communicates with ports 53 and 51 and tip 54. Venous return line 52 may be constructed in a manner per se known for venous introducer catheters. Tubing 49 may comprise a suitable length of a biocompatible material, such as silicone. Alternatively, tubing 49 may be omitted and blood outlet port 48 of catheter 41 and blood inlet port 51 of venous return line 52 may be lengthened to engage either end of filter 50 or each other.

Figure 3B:
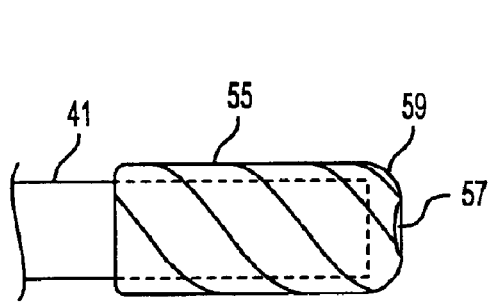
Figure 3C:
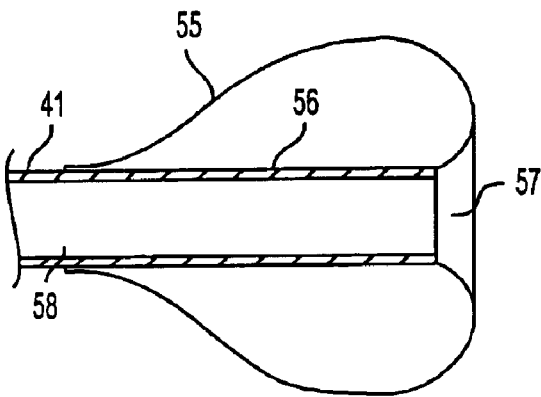

With respect to FIGS. 3B and 3C, distal occlusive element 42 comprises expandable funnel-shaped balloon 55. In accordance with manufacturing techniques which are known in the art, balloon 55 comprises a compliant material, such as polyurethane, latex or polyisoprene which has variable thickness along its length to provide a funnel shape when inflated. Balloon 55 is affixed to distal end 56 of catheter 41 in an inverted fashion, for example, by gluing or a melt-bond, so that opening 57 in balloon 55 leads into aspiration lumen 58 of catheter 41. Balloon 55 preferably is wrapped and heat treated during manufacture so that distal portion 59 of the balloon extends beyond the distal end of catheter 41 and provides an atraumatic tip or bumper for the catheter.

Figure 3D:
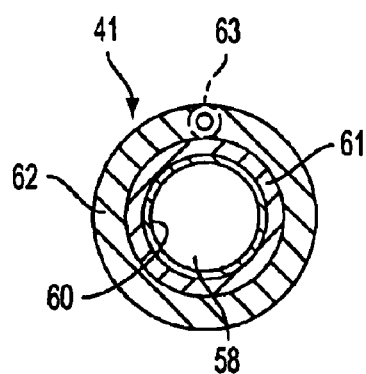

As shown in FIG. 3D, catheter 41 preferably comprises inner layer 60 of low-friction material, such as polytetrafluoroethylene ("PTFE"), covered with a layer of flat stainless steel wire braid 61 and polymer cover 62 (e.g., polyurethane, polyethylene, or PEBAX). Inflation lumen 63 is disposed within polymer cover 62 and couples inflation port 44 to balloon 55.

Referring to FIG. 4, alternative embodiments for wire 45 and balloon 46 of FIG. 3A are described for use in occluding a communicating artery, e.g., the external carotid artery. In FIG. 4A, occlusive device 121 comprises proximal hub 120, hypo tube 127, shaft 128, balloon 136 and coil 142. Hypo tube 127 preferably comprises stainless steel, while shaft 128 preferably comprises a radiopaque material. Balloon 136 is configured using a tubular balloon material, e.g., chronoprene, that is compliant in nature and provides a self-centering balloon when deployed. The proximal end of balloon 136 is secured to radiopaque shaft 128 by band 132 and taper 130. The distal end of balloon 136 is affixed to coil 142 via taper 140.

Core wire 122 is slidably disposed within hypo tube 127 so that its proximal end is disposed in proximal hub 120 and its distal end is affixed to taper 140. Fluid may be injected into the annulus surrounding core wire 122 so that the fluid exits into balloon 136 via inflation window 134, thus permitting balloon 136 to expand radially and longitudinally. Core wire 122, taper 140 and coil 142 may move distally to accommodate such linear extension. Stroke limiter 123, disposed on the distal end of core wire 122, ensures that balloon 136 does not extend longitudinally more a predetermined distance 'x'.

In the alternative embodiment of FIG. 4B, occlusive device 151 comprises shaft 152, balloon 158, and coil 168. Shaft 152 preferably comprises a radiopaque material and connects to a hypo tube similar to that of FIG. 4A. The proximal components for device 151, i.e., proximal to shaft 152, are the same as the components that are proximal to shaft 128 in FIG. 4A.

Balloon 158 is constrained at its proximal end by band 156 having proximal balloon marker 157. Taper 154 is provided on the proximal end of band 156 in alignment with the proximal end of balloon 158. The distal end of balloon 158 is everted, as shown in FIG. 4B, and secured with radiopaque band 160 that provides a fluoroscopic reference for the distal boundary of the balloon. Taper 164 further secures the everted distal section, sandwiching between the first and second folds.

Core wire 150 is affixed distally to coil 168 having radiopaque marker 170. Lumen 159 communicates with an inflation port (not shown) at its proximal end and with inflation window 166 at its distal end. Lumen 159 permits the injection of fluids, e.g., saline, to deploy balloon 158. Core wire 150 is slidably disposed in the hypo tube and shaft 152 to prevent extension of balloon 158 up to a distance 'x', as indicated in FIG. 4A.

Referring to FIG. 5, apparatus suitable for removing thrombi are described. In FIG. 5A, thrombectomy wire 200 having proximal and distal ends and atraumatic tip 202 affixed to the distal end is depicted in a contracted state within coil 204. Atraumatic tip 202 preferably comprises a ball-shape having a larger diameter than wire 200, as shown in FIG. 5A. In a preferred embodiment, thrombectomy wire 200 comprises a shape-memory retaining material, for example, a Nickel Titanium alloy (commonly known in the art as Nitinol).

The use of Nitinol generally requires the setting of a custom shape in a piece of Nitinol, e.g., by constraining the Nitinol element on a mandrel or fixture in the desired shape, and then applying an appropriate heat treatments, which are per se known.

Coil 204 covers wire 200 along its length, up to atraumatic tip 202. As coil 204 is retracted proximally, wire 200 self-expands to a predetermined knot configuration, as shown in FIG. 5B. In a preferred embodiment, the diameter of wire 200 is about 0.002 inches, the diameter of atraumatic tip 202 is about 0.014 inches, and coil 204 is manufactured using platinum. It should be appreciated that an outer sheath may be used in place of coil 204, such that proximally retracting the outer sheath causes wire 200 to self-deploy.

Figure 5A:
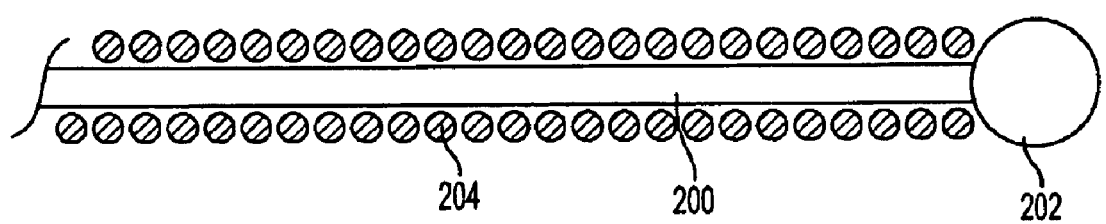
FIGS. 5A–5F depict thrombectomy wires having shape memory properties in contracted and deployed states.
Figure 5B:
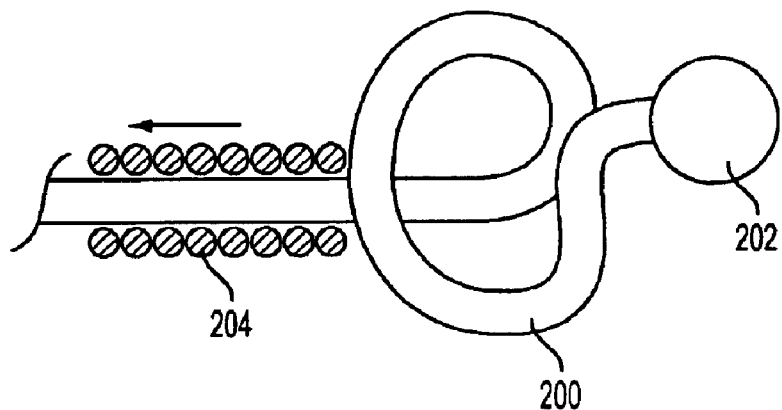
Figure 5C:
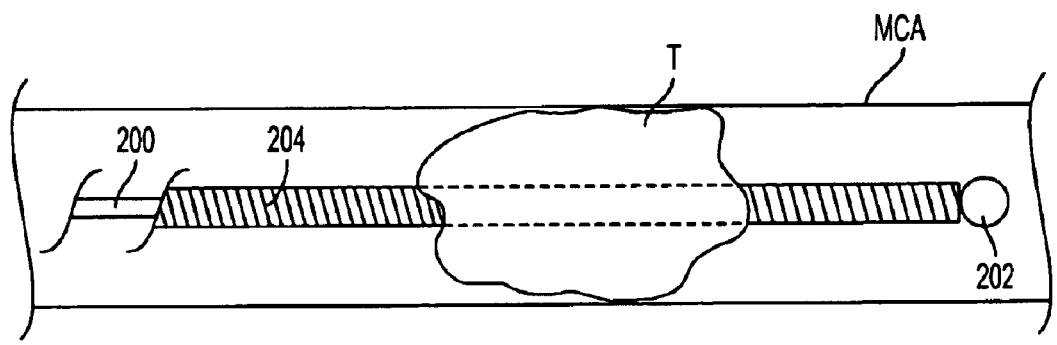

Referring to FIG. 5C, a method for using thrombectomy wire 200 to snare a thrombus T, e.g., in middle cerebral artery MCA, is described. Thrombectomy wire 200, initially contracted within coil 204, is advanced through a lumen of catheter 2, then preferably is advanced in retrograde fashion via the ICA to the site of the cerebral lesion in the MCA. Under controlled flow conditions, i.e., conditions that will promote the flow of emboli toward catheter 2, atraumatic tip 202 and coil 204 pierce thrombus T, as shown in FIG. 5C.

Figure 5D:
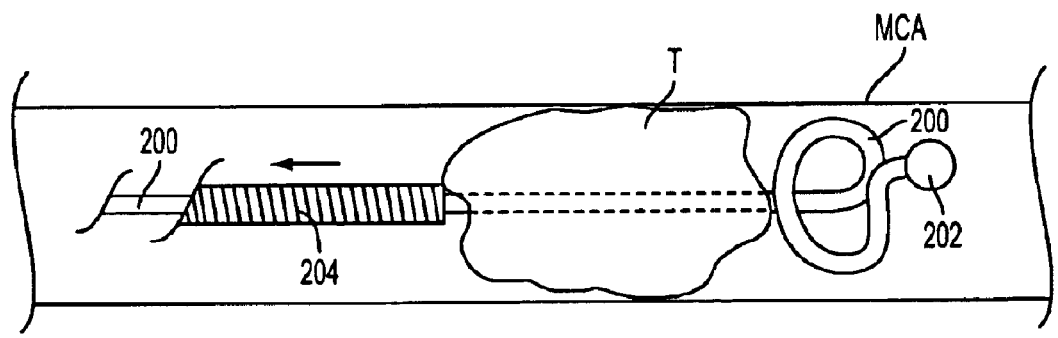

Coil 204 then is retracted proximally with respect to wire 200 to self-deploy shape memory wire 200 at a location distal to thrombus T, as shown in FIG. 5D. Wire 200 then is retracted proximally to snare thrombus T, and atraumatic tip 202 of wire 200 facilitates removal of the lesion.

Figure 5E:
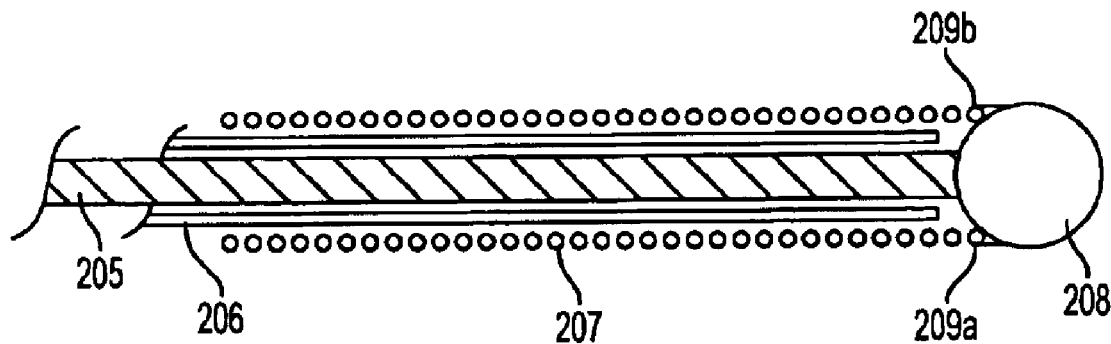
Figure 5F:
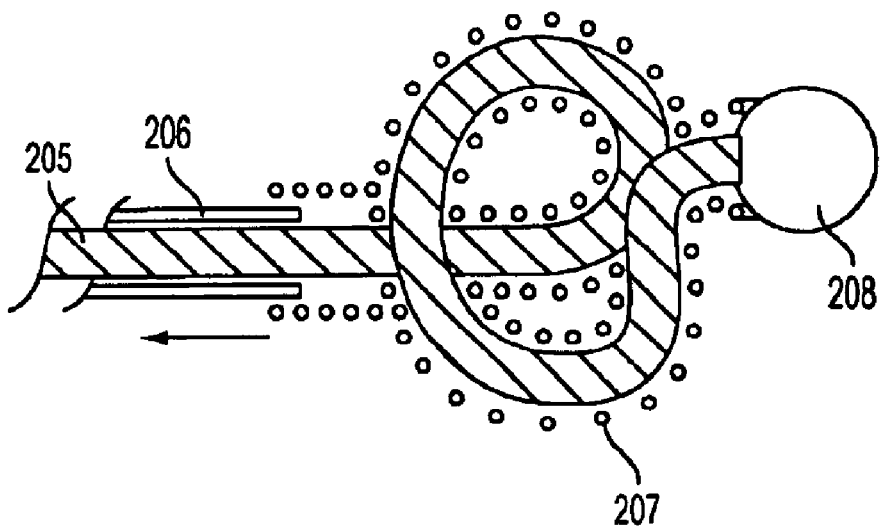

Referring to FIGS. 5E–5F, an alternative embodiment a thrombectomy wire of FIGS. 5A–5B is described. In FIG. 5E, thrombectomy wire 205 having atraumatic tip 208 is delivered in a contracted state within slidable sheath 206. Thrombectomy wire 205 is configured to self-deploy to a predetermined shape, e.g., via use of a shape memory material, upon proximal retraction of sheath 206. Coil 207 overlays slidable sheath 206 and is affixed to atraumatic tip 208 at points 209a and 209b, e.g., via a solder or weld. Sheath 206 initially is provided in a distalmost position such that it abuts atraumatic tip 208 and constrains wire 205 along its length. Sheath 206 advantageously enhances the distal pushability of the device, particularly when the device is advanced though an occlusion.

Upon positioning the distal end of wire 205 at a location distal to the occlusion, sheath 206 is retracted proximally to cause wire 205 to self-deploy, preferably to a knot-shaped configuration, as depicted in FIG. 5F. Coil 207, affixed to atraumatic tip 208 of wire 205, conforms to the shape of wire 205. The deployed knot-shaped device then is proximally retracted to snare the occlusion, according to methods described hereinabove.

Referring to FIG. 6, alternative apparatus suitable for removing thrombi are described. In FIG. 6A, thrombectomy wire 300 having proximal and distal ends and atraumatic tip 302 affixed to the distal end is depicted in a contracted state within outer sheath 306, also having proximal and distal ends. In a preferred embodiment, thrombectomy wire 300 comprises a shape-memory retaining material, for example, Nitinol, which may heat treated according to techniques described hereinabove. Accordingly, when outer sheath 306 is retracted proximally, a distal section of wire 300 self-expands, preferably to a predetermined knot-shaped configuration, as shown in FIG. 6B.

Coil 304 preferably is disposed about a distal section of wire 300 that comprises a smaller diameter relative to a proximal section of wire 300, so that the addition of coil 304 does not increase the distal profile of wire 300 with respect to the proximal section. Coil 304 preferably is affixed to wire 300 at a proximal end and further affixed to wire 300 and/or atraumatic tip 302 at a distal end.

Figure 6A:
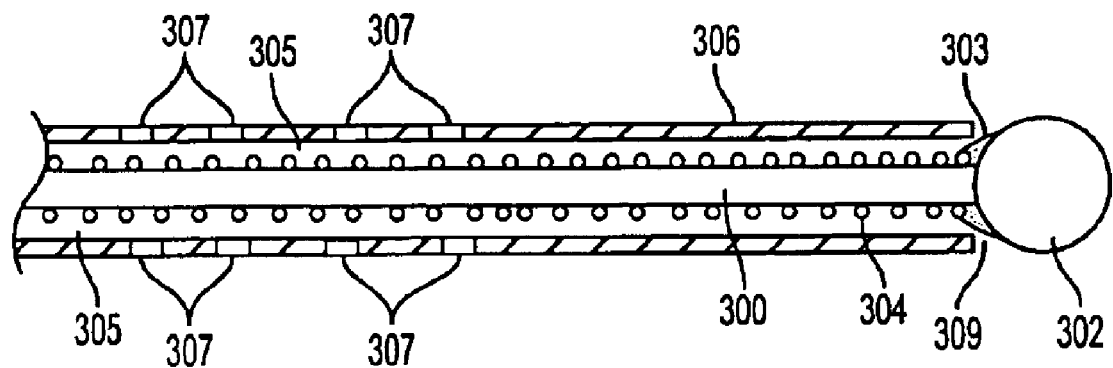
FIGS. 6A–6D describe apparatus comprising a thrombectomy wire having drug delivery capabilities.
Figure 6B:
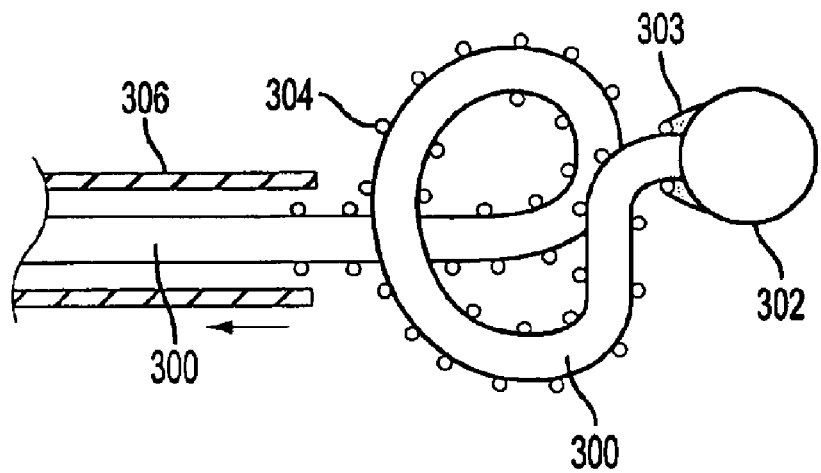

Outer sheath 306 preferably comprises at least one drug delivery port 307 disposed in a lateral surface of outer sheath 306. Drug delivery port 307 more preferably is disposed near the distal end of outer sheath 306, as shown in FIG. 6A. An annulus formed between wire 300 and an inner wall of sheath 306 forms drug delivery lumen 305. Drug delivery lumen 305 is sized to permit the injection of lytic agents to the distal end of outer sheath 306, without providing so much space as to allow wire 300 to assume its predetermined deployed shape. Additionally, drug delivery port 309, which forms a space between the distal end of sheath 306 and atraumatic tip 302, may be used to deliver lytic agents to a treatment site, preferably when atraumatic tip 302 is disposed substantially within a stenosis.

Figure 6C:
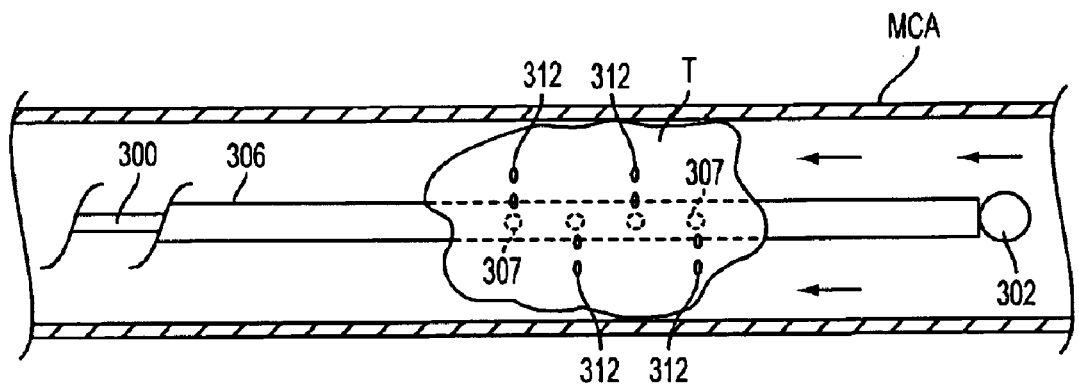

Referring to FIG. 6C, a method for using thrombectomy wire 300 in conjunction with outer sheath 306 to remove a thrombus T, e.g., located in middle cerebral artery MCA, is described. Thrombectomy wire 300, which initially is provided in a contracted state within outer sheath 306, is advanced through a lumen of catheter 2, then preferably is advanced in retrograde fashion via the internal carotid artery to the site of the cerebral lesion in the MCA. Under controlled flow conditions, i.e., conditions that will promote the flow of emboli toward catheter 2, atraumatic tip 302 then pierces thrombus T, and wire 300 and sheath 306 may be advanced distally beyond thrombus T, as shown in FIG. 6C.

Outer sheath 306 preferably is positioned so that at least one drug delivery port 307 is disposed within thrombus T, as shown in FIG. 6C. At this time, lytic agents 312 may be introduced into drug delivery lumen 305, e.g., via a proximal port (not shown) that is in fluid communication with the proximal end of outer sheath 306. Lytic agents 312 are advanced toward the distal end of sheath 306, and may exit sheath 306 through drug delivery port 307 so that they are infused into thrombus T, as shown in FIG. 6C. Alternatively, atraumatic tip 302 and the distal end of outer sheath 306 may be disposed substantially within thrombus T, and lytic agents 312 may be delivered to thrombus T via drug delivery port 309 of FIG. 6A.

Figure 6D:
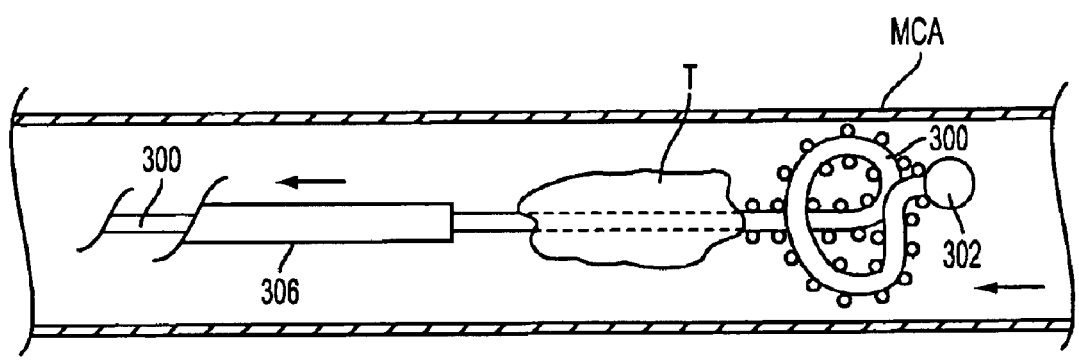

Lytic agents 312 may partially or fully disrupt thrombus T, and any emboli generated during the lytic process is carried toward catheter 2 via the controlled flow previously established in the region. With thrombus T having been at least partially disrupted, outer sheath 306 then may be retracted proximally with respect to wire 300 to self-deploy wire 300 at a location distal to thrombus T, as shown in FIG. 6D. Wire 300 then is retracted proximally to snare a remaining portion of thrombus T, and atraumatic tip 302 of wire 300 facilitates removal of the lesion.

Referring now to FIG. 7, a preferred method for using the apparatus described hereinabove to treat stroke, in accordance with principles of the present invention, is described.

Referring to FIG. 7A, catheter 404 of FIG. 3A is positioned in the common carotid artery CCA using guide wire 406. Catheter 404 is positioned proximal of the carotid bifurcation, as shown, preferably in the hemisphere in which the cerebral occlusion is located. Balloon 408, for example, as described hereinabove with respect to FIG. 4, then may be disposed in the external carotid artery ECA and deployed, as shown in FIG. 7B. Alternatively, if the ECA is already substantially occluded due to an existing lesion, then the use of balloon 408 may be omitted.

Referring to FIG. 7C, distal occlusive element 412 of catheter 404 is deployed to occlude antegrade flow in the selected CCA. Venous return catheter 52 of FIG. 3A then is placed in a remote vein, such that negative pressure in venous return catheter 52 during diastole establishes a continuous flow through the lumen of catheter 404. This induces retrograde flow in the ICA, as depicted in FIG. 7C. Thrombectomy wire 414, for example, as described with respect to FIG. 6 hereinabove, then may be advanced through catheter 404 and into the cerebral vasculature via the ICA.

Figure 7D:
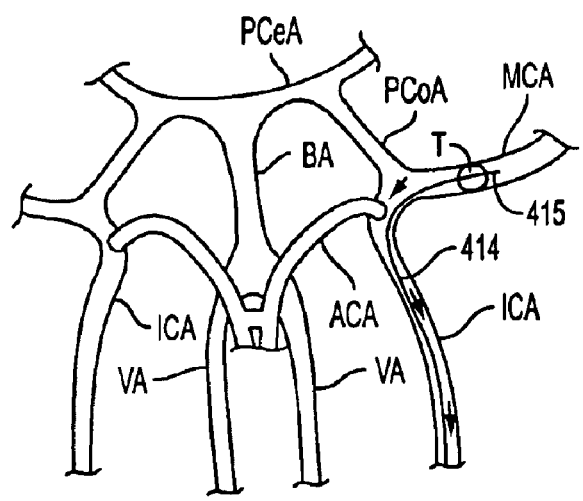

Referring to FIG. 7D, a view of the cerebral vasculature under the conditions described in FIG. 7C is shown. Thrombectomy wire 414 has been advanced to a location just proximal of thrombus T, for example, in middle cerebral artery MCA. The continuous flow through the lumen of catheter 404 that induces retrograde flow in the ICA also influences flow in the MCA, as depicted in FIG. 7D, such that flow in the MCA is toward the aspiration lumen of catheter 404.

The distal end of thrombectomy wire 414 may be advanced distally across thrombus T, as shown in FIG. 7D. Thrombectomy wire 414 preferably is advanced across thrombus T in a contracted state within outer sheath 415 having proximal and distal ends. In FIG. 7D, thrombectomy wire 414 and outer sheath 415 preferably are constructed in accordance with thrombectomy wire 300 and outer sheath 306 of FIG. 6, respectively. Outer sheath 415 preferably comprises at least one drug delivery port disposed in a lateral surface near the distal end.

In a preferred method, the distal end of outer sheath 415 crosses thrombus T, as shown in FIG. 7D, and the drug delivery port of outer sheath 415 is positioned within thrombus T. Lytic agents then may be delivered to thrombus T via the drug delivery port. Alternatively, the distal end of outer sheath 415 may be positioned substantially within thrombus T, and lytic agents may be delivered to thrombus T via port 309 of FIG. 6A.

Figure 7E:
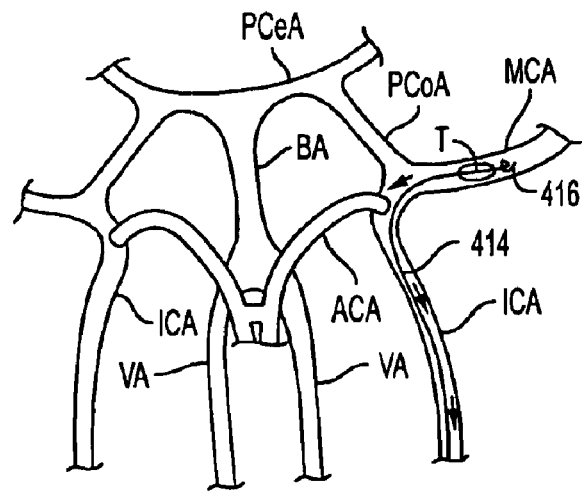

The introduction of lytic agents via outer sheath 415 may be used to at least partially dislodge thrombus T, as shown in FIG. 7E. After delivering the lytic agents for the desired time, the distal end of outer sheath 415 is positioned distal to thrombus T. Outer sheath 415 then is retracted proximally to self-deploy deployable knot 416 of wire 414 at a location distal to thrombus T, as shown in FIG. 7E.

Deployable knot 416 of thrombectomy wire 414 then may be retracted proximally to snare any remaining portion of thrombus T, as shown in FIG. 7E, and then is retracted into catheter 404. Any emboli generated during the procedure will be directed into catheter 404 via the established retrograde flow. Distal occlusive element 412 and external carotid occlusive device 408 then are contracted, and catheter 404 may be removed from the patient.

It should be noted that the method steps described in FIG. 7 may be used in combination with any of the apparatus described hereinabove. For example, stoke treatment in accordance with the present invention may be performed primarily using emboli removal catheter 404 disposed in the common carotid artery to influence cerebral flow. Alternatively, emboli removal catheter 404 of the present invention may be used in combination with occlusive element 408 disposed in an external carotid artery. Additionally, the proximal end of emboli removal catheter 404 may be coupled to a syringe (not shown) that communicates with the lumen of emboli removal catheter 404, so that the syringe may be used to influence the aspiration through emboli removal catheter 404, which in turn influences cerebral flow.

In yet a further alternative embodiment, a recovery catheter, i.e., a micro catheter, may be advanced through catheter 404 and via the ICA to a location in closer proximity to the cerebral occlusion. Such an embodiment is described in detail in commonly assigned, co-pending U.S. patent application Ser. No. 09/972,225. Alternatively, thrombectomy wire 414 may be replaced using a thrombectomy wire that rotationally engages and removes thrombus T, as opposed to snaring thrombus T. Such an embodiment also is described in detail in the above-referenced, co-pending application.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. Apparatus suitable for treating stroke by removing thrombus from a vessel, the apparatus comprising:

a catheter having proximal and distal ends, a lumen extending therebetween, and an inflatable occlusive element disposed on the distal end, the inflatable occlusive element having a contracted position suitable for transluminal insertion and an expanded position wherein the inflatable occlusive element occludes antegrade flow in the vessel;

a sheath disposed for translation through the lumen of the catheter, the sheath having an interior passageway;

a thrombectomy wire consisting of a deployable wire disposed within the interior passageway and having proximal and distal ends, the distal end having a contracted state when disposed within the interior passageway and a deployed state when extended from the interior passageway, wherein the deployable wire is adapted to be inserted into the vessel in the contracted state, and wherein the distal end self-deploys to a predetermined shape in the deployed state, the predetermined shape adapted to engage and remove the thrombus; and means, coupled to the proximal end of the catheter, for inducing retrograde flow through the lumen.

2. The apparatus of claim 1 further comprising:

a shaft having proximal and distal ends; and a balloon having proximal and distal ends, the balloon being disposed near the distal end of the shaft.

3. The apparatus of claim 2 wherein the balloon is adapted to be disposed in a communicating artery.

4. The apparatus of claim 2 wherein the distal end of the balloon is everted.

5. The apparatus of claim 1 wherein an annulus between the deployable wire and an inner surface of the interior passageway of the sheath defines a drug delivery lumen.

6. The apparatus of claim 5 wherein the deployable wire further comprises an atraumatic tip affixed to the distal end.

7. The apparatus of claim 6 wherein a space between a distal end of the sheath and the atraumatic tip defines a drug delivery port, wherein the drug deliver port is in fluid communication with the drug delivery lumen.

8. The apparatus of claim 5 wherein the sheath comprises at least one drug delivery port disposed in a lateral surface of the sheath, wherein the drug delivery port is in fluid communication with the drug delivery lumen.

9. The apparatus of claim 5 wherein a distal section of the deployable wire comprises a smaller diameter relative to a proximal section of the deployable wire.

10. The apparatus of claim 9 wherein the deployable wire further comprises a coil disposed about a portion of the distal section.

11. The apparatus of claim 5 wherein the drug delivery lumen is configured to permit the delivery of at least one lytic agent to a distal end of the sheath.

12. The apparatus of claim 5 wherein the distal end of the deployable wire comprises a knot shape in the deployed state.

13. The apparatus of claim 5 wherein the deployable wire is substantially flush with an inner wall of the cerebral vessel in the deployed state.

14. The apparatus of claim 1 wherein the deployable wire comprises a shape-memory material.

15. The apparatus of claim 1 wherein the catheter further comprises an inflation lumen extending between the proximal and distal ends, the inflation lumen having a distal end coupled to the inflatable occlusive element and a proximal end adapted to be coupled to an inflation source.

16. The apparatus of claim 1 wherein the predetermined shape of the distal end of the deployable wire forms a helical coil.

17. The apparatus of claim 1 wherein the means for inducing retrograde flow through the lumen comprises a venous return catheter having first and second ends, the first end configured to be coupled to the proximal end of the catheter and the second end configured for placement in a remote vein.

18. The apparatus of claim 17 further comprising a filter configured to be interposed between the first end of the venous return catheter and the proximal end of the catheter.

19. A stroke treatment apparatus comprising:

a catheter having a proximal end and a distal region, a lumen extending therebetween;

an occlusive element disposed on the distal region of the catheter, the occlusive element having a contracted state and a deployed state;

a sheath disposed for translation in the lumen of the catheter, the sheath having an interior passageway;

a thrombectomy wire consisting of a deployable wire disposed within the interior passageway of the sheath, the deployable wire having a distal end having a contracted state when disposed with the interior passageway and a deployed state when extended from the sheath, the distal end adapted to engage and disrupt an occlusion in the deployed state; and a venous return catheter having first and second ends, the first end configured to be coupled to the proximal end of the catheter and the second end configured for placement in a remote vein.

20. The stroke treatment apparatus of claim 19, wherein an annulus formed between the deployable wire and the sheath defines a drug delivery lumen for delivering a lytic agent to the occlusion.

21. The stroke treatment apparatus of claim 19, wherein the distal end of the deployable wire self-deploys to a helical shape in the deployed state.

22. The apparatus of claim 19 further comprising a filter configured to be interposed between the first end of the venous return catheter and the proximal end of the catheter.

* * * * *